(12) United States Patent
Kayan

(10) Patent No.: US 7,229,452 B2
(45) Date of Patent: Jun. 12, 2007

(54) TACK AND TACK APPLIER

(75) Inventor: Helmut Kayan, Redwood City, CA (US)

(73) Assignee: Tyco Healthcare Group LP, Norwalk, CT (US)

( * ) Notice: Subject to any disclaimer, the term of this patent is extended or adjusted under 35 U.S.C. 154(b) by 444 days.

(21) Appl. No.: 10/421,170

(22) Filed: Apr. 22, 2003

(65) Prior Publication Data

US 2004/0133214 A1 Jul. 8, 2004

Related U.S. Application Data

(60) Provisional application No. 60/374,672, filed on Apr. 22, 2002.

(51) Int. Cl.
*A61B 17/10* (2006.01)
(52) U.S. Cl. .................. 606/142; 411/451.1; 227/179.1
(58) Field of Classification Search ........ 606/138–144, 606/213, 219–221, 228, 232–233; 227/175.1, 227/176.1, 179.1; 411/439, 451.1–451, 457
See application file for complete search history.

(56) References Cited

U.S. PATENT DOCUMENTS

| | | | |
|---|---|---|---|
| 3,435,526 A | 4/1969 | Brancato | |
| 3,638,654 A | 2/1972 | Akuba | |
| 3,858,783 A | 1/1975 | Kapitanov et al. | |
| 3,870,048 A | 3/1975 | Yoon | |
| RE28,932 E | 8/1976 | Noiles et al. | |
| 4,204,541 A | 5/1980 | Kapitanov | |
| 4,235,246 A | 11/1980 | Weiss | |
| 4,340,331 A * | 7/1982 | Savino | 411/457 |
| 4,357,946 A | 11/1982 | Dutcher et al. | |
| 4,406,363 A | 9/1983 | Aday | |
| 4,448,194 A | 5/1984 | DiGiovanni et al. | |
| 4,593,843 A | 6/1986 | Saravis | |
| 4,595,007 A | 6/1986 | Mericle | |
| 4,596,350 A | 6/1986 | Smith et al. | |
| RE32,227 E | 8/1986 | Dutcher | |
| 4,616,638 A | 10/1986 | Griggs | |
| 4,627,437 A | 12/1986 | Bedi et al. | |
| 4,628,943 A | 12/1986 | Miller | |
| 4,643,190 A | 2/1987 | Heimberger | |
| 4,838,254 A | 6/1989 | Guathier | |
| 4,850,355 A | 7/1989 | Brooks et al. | |
| 4,858,601 A | 8/1989 | Glisson | |
| 4,887,601 A * | 12/1989 | Richards | 606/219 |

(Continued)

FOREIGN PATENT DOCUMENTS

BE 1006874 A6 1/1995

(Continued)

*Primary Examiner*—Michael J. Hayes
*Assistant Examiner*—M. Thomas Andersen

(57) ABSTRACT

A surgical tack is disclosed for securing a surgical mesh material to body tissue. The tack includes a pair of legs and an arcuate cross-member. A surgical tack applier is also disclosed, for applying the surgical tack. The applier includes an elongate tubular portion having a jacket with a main channel and a pair of longitudinally extending sub channels. A rotatable drive rod having a helical thread is coupled to the applier, and the sub channels receive the legs of the tack. The helical thread receives the arcuate cross-member of the surgical tack. Rotation of the drive rod drives the tack from the distal end of the applier.

18 Claims, 5 Drawing Sheets

U.S. PATENT DOCUMENTS

| | | |
|---|---|---|
| 4,950,276 A | 8/1990 | Vince |
| 4,976,715 A | 12/1990 | Bays et al. |
| 5,002,562 A * | 3/1991 | Oberlander ............... 606/221 |
| 5,007,921 A | 4/1991 | Brown |
| 5,018,530 A | 5/1991 | Rank et al. |
| 5,053,047 A | 10/1991 | Yoon |
| 5,100,420 A | 3/1992 | Green et al. |
| 5,171,247 A | 12/1992 | Hughett et al. |
| 5,171,249 A | 12/1992 | Stefanchik et al. |
| 5,203,864 A | 4/1993 | Phillips |
| 5,217,486 A | 6/1993 | Rice et al. |
| 5,222,976 A | 6/1993 | Yoon |
| 5,228,565 A | 7/1993 | Sinn |
| 5,242,457 A | 9/1993 | Akopov et al. |
| 5,258,000 A | 11/1993 | Gianturco |
| 5,259,395 A | 11/1993 | Li |
| 5,269,792 A | 12/1993 | Kovac et al. |
| 5,271,543 A | 12/1993 | Grant et al. |
| 5,282,807 A | 2/1994 | Knoepfler |
| 5,295,956 A | 3/1994 | Bales et al. |
| 5,297,714 A | 3/1994 | Kramer |
| 5,306,281 A | 4/1994 | Beurrier |
| 5,309,617 A | 5/1994 | Dannar |
| 5,309,927 A | 5/1994 | Welch |
| 5,312,024 A | 5/1994 | Grant et al. |
| 5,318,575 A | 6/1994 | Chesterfield et al. |
| 5,320,630 A | 6/1994 | Ahmed |
| 5,330,503 A | 7/1994 | Yoon |
| 5,342,395 A | 8/1994 | Jarrett et al. |
| 5,350,400 A * | 9/1994 | Esposito et al. ............ 606/219 |
| 5,354,292 A | 10/1994 | Braeuer et al. |
| 5,356,064 A | 10/1994 | Green et al. |
| 5,356,424 A | 10/1994 | Buzerak et al. |
| 5,382,260 A | 1/1995 | Dormandy, Jr. et al. |
| 5,411,522 A | 5/1995 | Trott |
| 5,433,721 A | 7/1995 | Hooven et al. |
| 5,437,266 A | 8/1995 | McPherson et al. |
| 5,439,156 A | 8/1995 | Grant et al. |
| 5,452,836 A | 9/1995 | Huitema et al. |
| 5,454,834 A | 10/1995 | Boebel et al. |
| 5,465,895 A | 11/1995 | Knodel et al. |
| 5,487,500 A | 1/1996 | Knodel et al. |
| 5,488,958 A | 2/1996 | Topel et al. |
| 5,499,990 A | 3/1996 | Schülken et al. |
| 5,500,001 A | 3/1996 | Trott |
| 5,501,683 A | 3/1996 | Trott |
| 5,545,148 A | 8/1996 | Wurster |
| 5,582,616 A * | 12/1996 | Bolduc et al. ............... 606/143 |
| 5,607,436 A | 3/1997 | Pratt et al. |
| 5,626,613 A | 5/1997 | Schmieding |
| RE35,525 E | 6/1997 | Stefanchik et al. |
| 5,662,683 A | 9/1997 | Kay |
| 5,728,116 A | 3/1998 | Rosenman |
| 5,772,668 A | 6/1998 | Summers et al. |
| 5,782,844 A | 7/1998 | Yoon et al. |
| 5,797,931 A | 8/1998 | Bito et al. |
| 5,810,851 A | 9/1998 | Yoon |
| 5,810,882 A | 9/1998 | Bolduc et al. |
| 5,824,008 A | 10/1998 | Bolduc et al. |
| 5,830,221 A | 11/1998 | Stein et al. |
| 5,833,695 A | 11/1998 | Yoon |
| 5,904,696 A | 5/1999 | Rosenman |
| 5,941,890 A | 8/1999 | Voegele et al. |
| 5,964,772 A | 10/1999 | Bolduc et al. |
| 5,993,476 A | 11/1999 | Groiso |
| 6,036,701 A | 3/2000 | Rosenman |
| 6,059,787 A * | 5/2000 | Allen ........................ 606/75 |
| 6,063,070 A | 5/2000 | Eder |
| 6,099,537 A | 8/2000 | Sugai et al. |
| 6,113,611 A | 9/2000 | Allen et al. |
| 6,261,302 B1 | 7/2001 | Voegele et al. |
| 6,296,656 B1 | 10/2001 | Bolduc et al. |
| 6,402,765 B1 | 6/2002 | Monassevitch et al. |
| 6,425,903 B1 | 7/2002 | Voegele |
| 6,517,556 B1 * | 2/2003 | Monassevitch ............. 606/151 |
| 6,551,332 B1 | 4/2003 | Nguyen et al. |
| 6,551,333 B2 | 4/2003 | Kuhns et al. |
| 6,616,686 B2 * | 9/2003 | Coleman et al. ............ 606/219 |
| 6,638,297 B1 * | 10/2003 | Huitema ..................... 606/219 |
| 6,957,756 B2 * | 10/2005 | Lat et al. ...................... 227/83 |
| 2002/0065524 A1 | 5/2002 | Miller et al. |
| 2002/0068947 A1 | 6/2002 | Kuhns et al. |
| 2002/0087170 A1 | 7/2002 | Kuhns et al. |
| 2003/0105473 A1 | 6/2003 | Miller |

FOREIGN PATENT DOCUMENTS

| | | |
|---|---|---|
| DE | 295962 | 5/1916 |
| DE | 4304353 A1 | 4/1994 |
| EP | 0121362 A1 | 10/1984 |
| EP | 0324166 A2 | 7/1989 |
| EP | 0442482 A2 | 8/1991 |
| EP | 0554653 A2 | 8/1993 |
| EP | 0645149 A1 | 3/1995 |
| EP | 0648471 A1 | 4/1995 |
| EP | 0663184 A1 | 7/1995 |
| EP | 686373 A1 | 12/1995 |
| FR | 320731 | 4/1902 |
| FR | 2299548 | 8/1976 |
| FR | 2377796 | 8/1978 |
| GB | 2148232 A | 5/1985 |
| WO | WO90/14795 | 12/1990 |
| WO | WO93/16644 | 9/1993 |
| WO | WO96/03925 | 2/1996 |

* cited by examiner

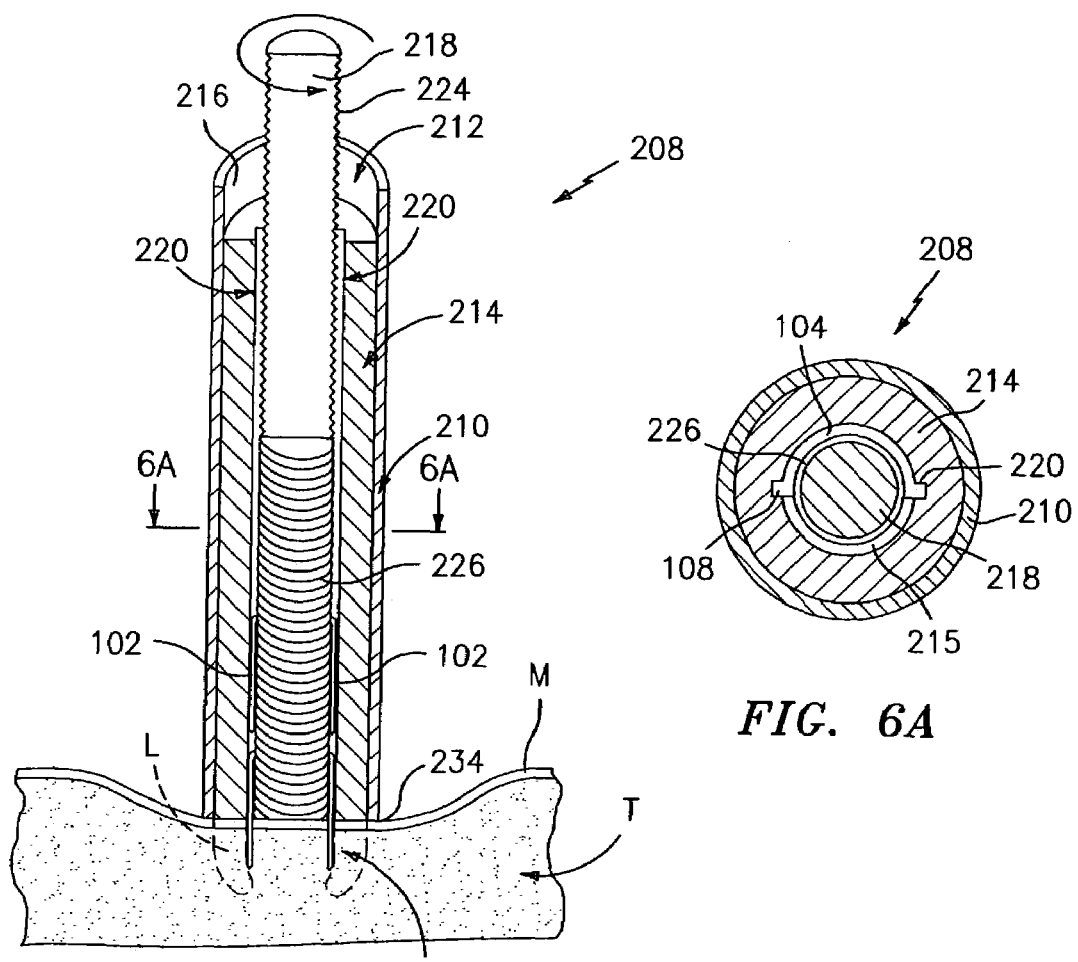
FIG. 6
FIG. 6A
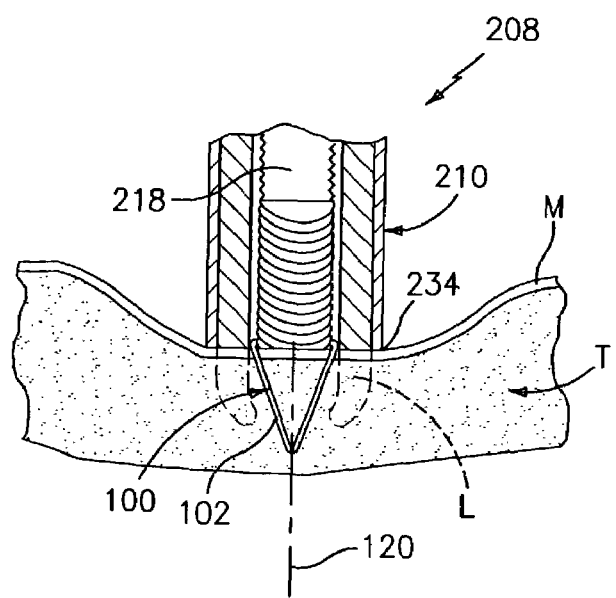
FIG. 7

TACK AND TACK APPLIER

CROSS REFERENCE TO RELATED APPLICATIONS

This application claims priority from and the benefits of U.S. provisional application No. 60/374,672 filed on Apr. 22, 2002.

BACKGROUND

1. Technical Field

The present disclosure relates to a novel tack and, more particularly to a low profile tack having deformable legs for securing a surgical mesh to body tissue. In addition, the present disclosure relates to a surgical tack applier and, more particularly to a surgical tack applier adapted to accommodate and apply a plurality of the surgical tacks of this disclosure.

2. Background of Related Art

A number of surgical procedures require instruments that are capable of applying a surgical fastener to tissue in order to form tissue connections or to secure objects to tissue. For example, during hernia repair it is often desirable to fasten a surgical mesh to the underlying body tissue. In certain hernias, such as direct or indirect inguinal hernias, a part of the intestine protrudes through a defect or an opening in the supporting abdominal wall to form a hernial sac. The opening can be repaired using an open surgical procedure where a relatively large incision is made in the patient and the hernia is closed outside the abdominal wall by suturing. Often, a mesh is attached with sutures over the opening to provide reinforcement.

Less invasive surgical procedures are currently available for hernia repair. In laparoscopic procedures, surgery is performed in the abdomen through a small incision, while in endoscopic procedures surgery is performed through narrow endoscopic tubes inserted through small incisions in the body. Laparoscopic and endoscopic procedures generally require long and narrow instruments capable of reaching deep within the body and configured to form a seal with the incision or tube through which they are inserted.

Currently, endoscopic techniques for hernia repair utilize fasteners, such as surgical staples or clips, to secure the mesh to the tissue thereby providing reinforcement of the repair and providing structure for the encouragement of tissue ingrowth. These staples or clips need to be compressed against the tissue and mesh in order to secure the two together thereby requiring a tool which is positioned on either side of the mesh and tissue in order to deform the staple or clip.

Another type of fastener suited for use in affixing mesh to tissue, during procedures such as hernia repair, is a coil fastener having a helically coiled body portion terminating in a tissue penetrating tip, in which the helical fastener is screwed into the mesh and body tissue. An example of this type of fastener is disclosed in U.S. Pat. No. 5,258,000 to Gianturco.

Yet another type of fastener suited for use in affixing surgical mesh to body tissue is a surgical tack that is driven through the surgical mesh and buried into the body tissue. In some embodiments, the tack comprises a pair of substantially parallel legs interconnected by a suture. Many different instruments for applying the surgical tacks through the surgical mesh and into the body tissue are known.

A need exists for a different surgical tack that firmly secures a surgical mesh to underlying body tissue and is readily removable without damaging the underlying tissue. A need exists for a tack having a low profile that when applied, is substantially in flush contact with the surface of the mesh. A need also exists for a tacking apparatus adapted for securing a surgical mesh to underlying body tissue utilizing the surgical tacks of the present disclosure. A need exists for such a tack applier, wherein each of a plurality of tacks can be applied with a single pull of a trigger, and for a tack applier that can apply a plurality of tacks seriatim through a replaceable tubular portion or jacket or cartridge.

SUMMARY

This invention is directed to a surgical tack for securing a mesh material to body tissue including a pair of legs where each leg has a proximal end and a free distal end. The legs of the surgical tack define a vertical plane. An arcuate cross-member is interconnected to the proximal ends of the legs and defines a centerline existing in the vertical plane where the centerline is substantially equidistant between the proximal ends of the legs and the arcuate cross-member defines a plane at an angle with respect to the vertical plane defined by the legs. The arcuate cross-member can be oriented substantially orthogonal to the vertical plane as defined by the pair of legs. The distal ends the legs can be provided with a pointed tip. The legs can be substantially parallel to one another and substantially parallel to the centerline. At least one leg of the legs does not have to be parallel to the centerline. The surgical tack can be made from a shape memory material or a bio-absorbable material, such as polyglycolic acid, polylactic acid, and polyglycolide.

The invention is also directed to a surgical fastener applier including a housing and an elongate tubular portion having a proximal end and a distal end. The elongate tubular portion further includes a bore therethrough and an elongate jacket having an inner surface defining a longitudinal main channel extending through the jacket, the main channel being adapted to receive a surgical tack having a pair of depending legs and an arcuate cross-member interconnecting proximal ends of the legs, the main channel having an inner surface that includes a pair of longitudinally extending sub channels formed along the inner surface, each of the pair of sub channels being adapted to receive at least a portion of a respective one of a pair of legs of the surgical fastener therein. A rotatable drive rod having a proximal end and a distal end extends axially through the jacket, the drive rod including a longitudinally extending helical thread, the helical thread defining a groove that is adapted to receive the arcuate cross-member of the surgical fastener therein. A mechanism is operatively connected to the drive rod for rotating the drive rod to drive fasteners, legs first, from the distal end of the drive rod and from the distal end of the tubular portion. The pair of sub channels of the jacket can be diametrically opposed. The jacket can include a plurality of pairs of sub channels formed along the inner surface where each pair of sub channels can be at least less than 180 degrees apart from one another. The mechanism can include a trigger pivotably coupled to the surgical applier. The applier may further include a mechanical deforming means operatively coupled to a distal end of the jacket, where the deforming means is adaptable to deflect the pair of legs of the surgical fastener toward one another as the surgical fastener is expelled from the distal end of the elongate tubular member. The mechanical deforming means can include radially inwardly directed lips.

This invention is further directed to a surgical fastener system including a surgical fastener having a pre-formed configuration and a formed configuration, the preformed configuration including a pair of legs and an arcuate cross-member interconnecting proximal ends of the legs and a surgical fastener applier including a housing having a reciprocating mechanism adapted for advancing the surgical fastener, an elongate tubular portion extending from the housing and having a bore therethrough, a jacket disposed within the bore and fixed to the elongate tubular portion, the jacket having an inner surface defining a longitudinally extending main channel extending therethrough and including a pair of longitudinally extending sub channels formed along the inner surface, each of the sub channels being configured and adapted to receive at least a portion of a respective one of a pair of legs of the surgical fastener in the pre-formed configuration therein, and a rotatable drive rod operatively coupled to the reciprocating mechanism and extending axially through the main channel of the jacket, the drive rod including a helical thread extending longitudinally along a length thereof, the helical thread defining a groove therein, the groove being adapted to receive the arcuate cross-member of the surgical fastener therein and, by rotating, to advance the surgical fastener distally through the tubular portion, the surgical fastener exiting the distal end of the tubular portion in the formed configuration. The drive rod can be adapted to receive a plurality of the surgical fasteners in the pre-formed configuration. The drive rod can be releasably attached to the reciprocating mechanism. The surgical fastener applier can be adapted and configured for releasably receiving a cassette, where the cassette can include a quantity of the surgical fasteners in the pre-formed configuration. The reciprocating mechanism may be a trigger pivotably coupled to the housing. The applier can have a distal end and a mechanical deforming means disposed at the distal end of the applier.

This invention is also directed to a surgical fastener applier including a housing, an elongate tubular portion having a proximal end and a distal end, the tubular portion having an elongate channel, the channel having an inner surface and a pair of longitudinally extending sub channels formed into and along the inner surface, each of the sub channels being adapted to receive at least a portion of a respective one of the legs of the surgical fastener therein, a rotatable drive rod having a proximal end and a distal end, the drive rod extending axially through the main channel, the drive rod including a longitudinally extending helical thread, the helical thread defining a groove that is adapted to receive the arcuate cross-member of the surgical fastener therein, and a mechanism operatively connected to the drive rod for rotating the drive rod to drive fasteners legs first from the distal end of the drive rod and from the distal end of the tubular portion. The pair of sub channels of the jacket can be diametrically opposed. The main channel can include a plurality of pairs of sub channels formed along the inner surface thereof, wherein each pair of sub channels can be at least less than 180 degrees apart from one another. The mechanism may include a trigger pivotably coupled to the surgical applier. The applier can include a mechanical deforming means operatively coupled to a distal end of the elongate tubular portion where the deforming means can be adapted to deflect the pair of legs of the surgical fastener toward one another as the surgical fastener is expelled from the distal end of the elongate tubular member. The mechanical deforming means can include radially inwardly directed lips.

It is an object of the present disclosure to provide a surgical tack that overcomes drawbacks of prior art surgical tacks.

It is an object of the present disclosure to provide a surgical tack which secures a surgical mesh to underlying body tissue and which is removable without damaging tissue.

It is another object of the present disclosure to provide a surgical tack with a low profile for substantially flush contact with the surface of the surgical mesh after installation.

It is another object of the present disclosure to provide a surgical tack applier that is adapted to apply the surgical tacks of the present disclosure to an operative site.

It is another object of the present disclosure to provide a surgical tack applier that is adapted to prevent rotation of a surgical tack as it is being expelled from the applier.

It is another object of the present disclosure to provide a tack that can be easily removed from tissue to which it has been applied.

These objects, together with other objects of the disclosure, are met by the tack and tack applier described, shown, and claimed herein.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

FIG. 6 is a partial cross-sectional perspective view of a distal end of the tack applier shown in FIG. 6 with a surgical tack, shown in FIG. 1, partially fired through a surgical mesh and into body tissue;

FIG. 6A is a top cross-sectional view of the distal end of the tack applier of FIG. 6 showing a single tack disposed in the channels;

FIG. 7 is a partial cross-sectional perspective view of a distal end of the tacker shown in FIG. 5 with a surgical tack shown in FIG. 1 completely fired into the surgical mesh and the body tissue;

DETAILED DESCRIPTION OF PREFERRED EMBODIMENTS

Figure 1:
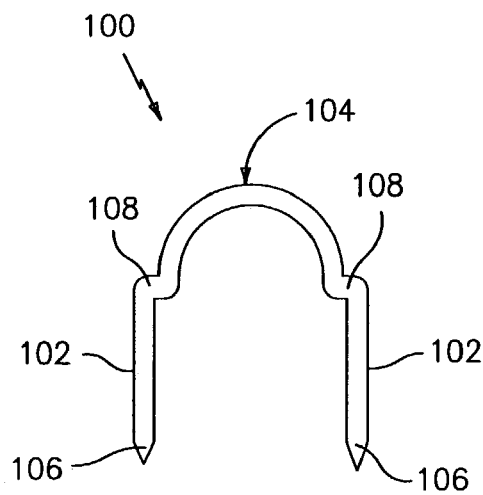
FIG. 1 is a top perspective view of a surgical tack in accordance with the present disclosure.

Preferred embodiments of the presently disclosed surgical tack will now be described in detail with reference to the drawing figures wherein like reference numerals identify similar or identical elements. Referring now in detail to FIGS. 1–4, a surgical fastener or tack in accordance with the present disclosure is generally designated as 100. As used herein, the term "distal" refers to that portion of the tack, tacker, or applier which is further from the user while the term "proximal" refers to that portion which is closer to the user.

Surgical tack 100 includes a pair of legs 102 and an arcuate cross-member 104 whose ends are interconnected to or joined with proximal ends 108 of legs 102. Legs 102 are substantially parallel to one another in a spaced apart relationship and each terminates at a distal end in a sharpened tip 106. While it is shown that each leg 102 has a generally circular cross-sectional profile, other cross-sectional profiles can be employed, e.g., rectangular, triangular, oval, etc. Although each tip 106 is shown as sharpened and conical, other tip profiles can be employed, e.g., rectangular, angled, rounded or the like. A centerline 120 bisects cross-member 104 and is substantially equidistant from the proximal ends of 108 of legs 102.

Arcuate cross-member 104 is oriented such that a plane defined by arcuate cross-member 104 is substantially orthogonal to the planes defined by respective legs 102. In particular, with reference to FIG. 3, the plane of arcuate cross-member 104 is disposed at an angle θ with respect to the plane defined between the pair of legs 102. In the preferred embodiment shown, angle θ is 90° such that the underlying surface of cross-member 104 can rest flush against a surgical mesh and underlying body tissue when surgical tack 100 is fully inserted into the same. Less preferably, the plane of cross-member 104 can be oriented at either an acute or an obtuse angle with respect to the plane defined by legs 102.

Figure 2:
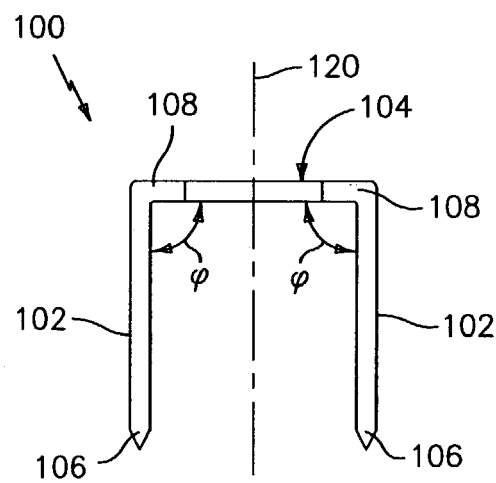
FIG. 2 is a front elevational view of the surgical tack shown in FIG. 1.
Figure 3:
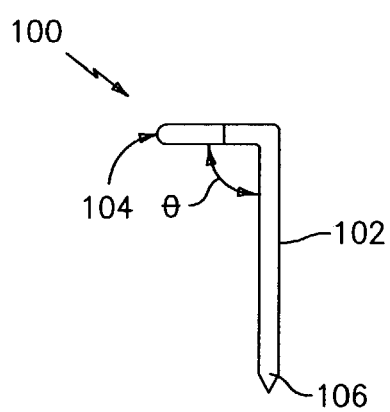
FIG. 3 is a side elevational view of the surgical tack shown in FIG. 1.
Figure 4:
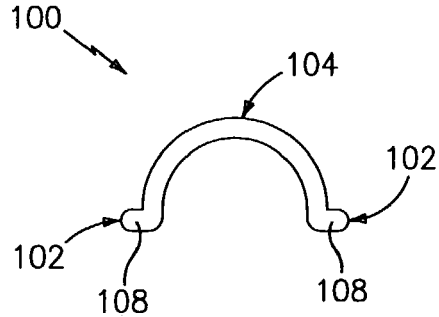
FIG. 4 is a top plan view of the surgical tack shown in FIG. 1.

As seen in FIG. 2, each leg 102 is disposed at an angle φ with respect to the plane of arcuate cross-member 104. In the preferred embodiment, angle φ is 90°. However, it is envisioned that the distal end of each leg 102 can be spaced further apart than the distance between proximal ends, 108 of legs 102 (i.e., having an angle φ greater than 90°), be spaced closer together than the distance between proximal ends 108 (i.e., having an angle φ less than 90°) or be shifted a distance laterally with respect to proximal ends 108 (i.e., having an angle φ of one leg which is less than 90° and an angle φ of the other leg which is greater than 90°).

It is contemplated in the preferred embodiment that surgical tack 100 is made from a semi-stiff pliable wire, such as titanium. Examples of other materials that can be used in constructing surgical tack 100 include titanium alloys, stainless steel, nickel, chrome alloys, and any other biocompatible implantable metals. Other options for materials include liquid crystal polymers such as polyglycolic acid, polylactic acid, and polyglycolide (poly(hydroxyacetic acid)) all of which are bioabsorbable materials. It may be desired to coat the surgical tack, or a portion thereof, with a biocompatible lubricious material that provides for easier delivery of the surgical tack into the body tissue.

It is further contemplated that surgical tack 100 can be made of a shape memory alloy. The surgical tack would have a pair of evenly spaced apart parallel legs while stored in the applying apparatus and, as the surgical tack contacts the warm body tissue or fluid during insertion, the shape memory of the surgical tack material would cause the pair of legs of the surgical tack to be drawn in toward one another. Alternately, the surgical tack made from the shape memory alloy could cause the pair of legs of the surgical tack to diverge apart from one another when the surgical tack contacts the warm body tissue or fluid during insertion.

Figure 5:
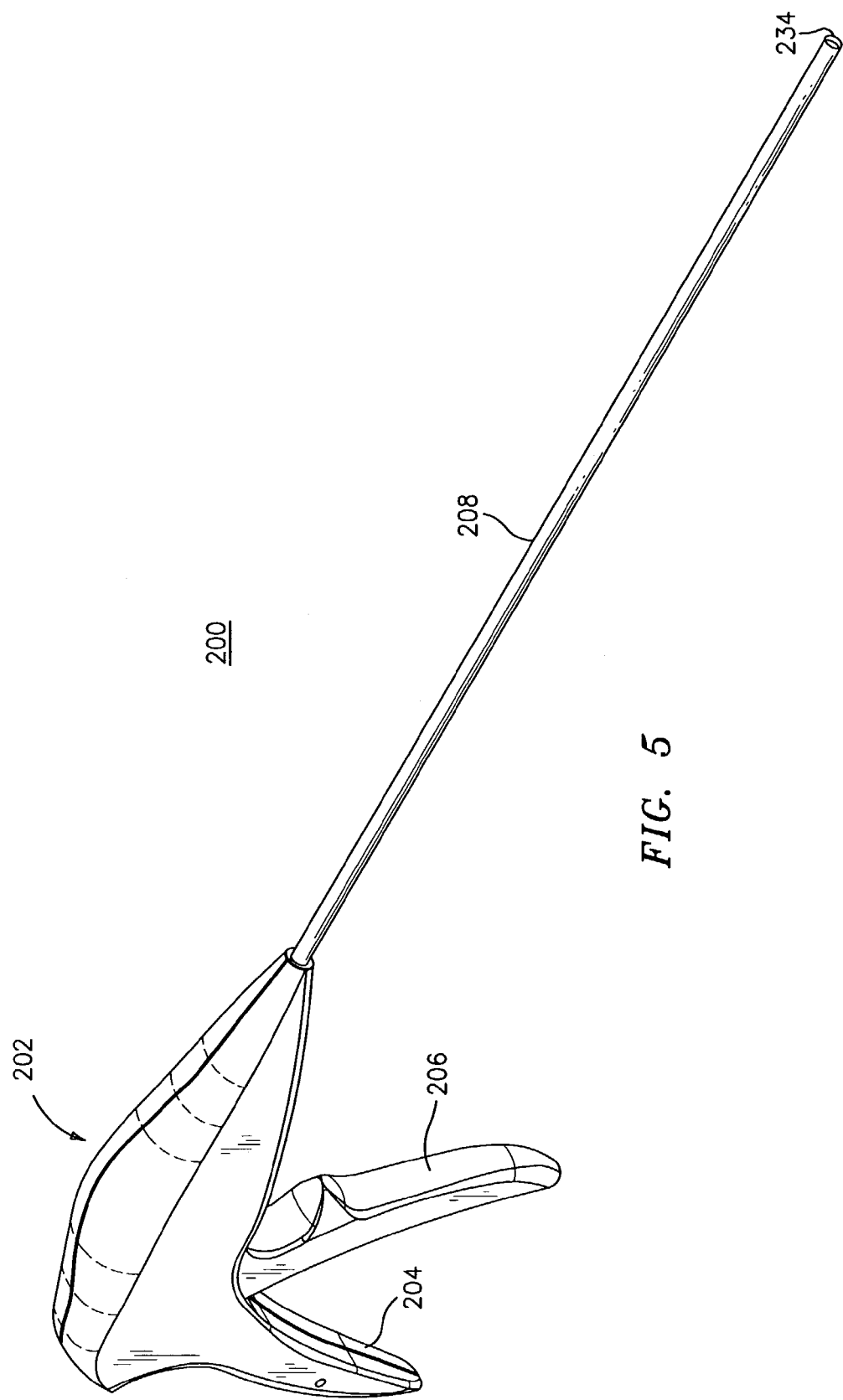
FIG. 5 is a perspective view of a preferred embodiment of a tack applier in accordance with the present disclosure.

With respect now to FIGS. 5–7 and initially with respect to FIG. 5, there is disclosed a preferred embodiment of a surgical tack applier generally designated 200. Surgical tack applier 200 is provided to secure a surgical mesh to tissue during surgical procedures such as hernia repair. Tack applier 200 generally includes a housing 202 and a handle portion 204 extending from housing 202. A trigger 206 is pivotably connected to housing 202 with a free end of trigger 206 spaced from a free end of handle portion 204.

Figure 5A:
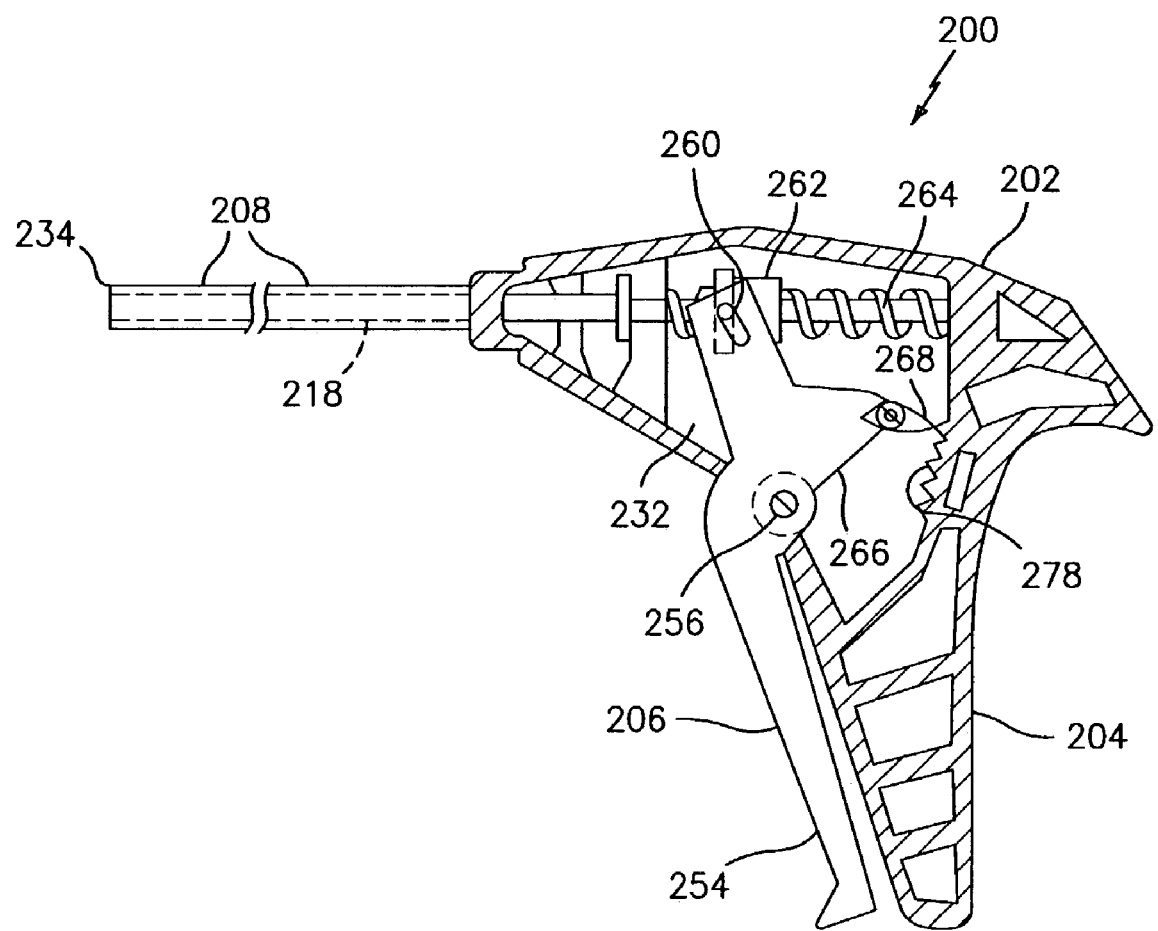
FIG. 5A is a side cross-sectional view of the tack applier of FIG. 5.

Tack applier 200 (FIG. 5A) further includes an elongated tubular portion 208 having a distal tip 234 and extending distally from housing 202. Elongated tubular portion 208 is provided to house or retain a plurality of surgical tacks 100, in accordance with the present disclosure, for application to body tissue. Elongated tubular portion 208 is preferably dimensioned to fit through conventional cannula structures used in hernia repair techniques. Proximal portion 202 includes handle portion 204 and an actuator 232 operably connected to a drive rod 218 disposed inside of elongated tubular portion 208 and having a plurality of surgical tacks 100 mounted therein. In general, through the manipulation of actuator 232, surgical tacks 100 are ejected, one by one, out of distal tip 234 and into body tissue. Tack applier 200, hereinafter described in more detail, is equally proficient in driving each of the embodiments of surgical tacks 100 set forth above into tissue. In the preferred embodiment of the proximal portion 202 of the tack applier, a trigger 206 is pivotally connected about a midpoint 256 to handle portion 204. A first end 254 of trigger 206 is to be configured for gripping by hand. A second end 260 of trigger 206 is to be adapted for pivotally engaging a nut driver 262.

Nut driver 262 of tack applier 200 travels upon a high helix lead screw 264 that is rotatably mounted within proximal portion 202. In the preferred embodiment, a longitudinal axis of high helix lead screw 264 is coaxial with a longitudinal axis extending through distal tip 234 of tack applier 200. Upon manipulation of trigger 206, nut driver 262 travels along lead screw 264 causing it to rotate. Through a connection of lead screw 264 to drive rod 218 (see FIG. 6), the action of lead screw 264 causes drive rod 218 to rotate. Lead screw 264 may be connected to drive rod 218 by any conventional means. For instance, lead screw 264 can have an internal bore receiving and engaging an end of drive rod 218. Further, the length of travel of nut driver 262 along lead screw 264 is chosen such that it causes the rotator to rotate a predetermined number of times so that with each full throw of trigger 206, one of the plurality of surgical tacks 100 is ejected from tack applier 200.

Additionally, in the preferred embodiment, trigger 206 further includes a midsection extension 266. Pivotally attached to midsection extension 266 of trigger 206 is contemplated to be a spring loaded pawl 268 adapted to releasably engage gear teeth 278 formed in the interior of handle portion 204. Spring loaded pawl 268 is configured to prohibit trigger 206 from backstroking until it has been completely depressed. Upon complete depression of trigger 206, pawl 268 clears gear teeth 278 and the spring biasing of pawl 268 rotates pawl 268 away from teeth 278, thereby allowing trigger 206 to return to its undepressed condition.

In operation, upon complete depression of trigger 206, nut driver 262 travels a pre-determined distance along lead screw 264, causing drive rod 218 to rotate a pre-determined number of revolutions corresponding to a number of turns needed to advance a particular distalmost surgical tack 100 from distal end 234 of tubular portion 208. As drive rod 218 rotates, surgical tacks 100 are retained in the groove of drive rod 218, advance distally in the groove of drive rod 218 toward distal end 234, and the most distal surgical tack 100 is threaded out of distal tip 234 of tack applier 200 and into tissue. Moreover, where trigger 206 is only partially depressed, spring loaded pawl 268 operates to hold trigger 206 stationary and will continue to function to hold trigger 206 stationary until trigger 206 has been completely depressed. In this way, the delivery of surgical tacks 100 into body tissue is controlled so that only one of the plurality of surgical tacks 100 may be completely ejected out of tack applier 200 and pressed into body tissue at a time.

In the preferred embodiment, proximal portion 202 is fabricated to have a reusable handle that can be re-sterilized, and tubular portion 208 is made disposable. Thus, upon discharge of all surgical tacks 100 from distal tip 234, tubular portion 208 can be discarded and replaced. The handle could be reused up to a limited number of procedures.

Referring now in particular to FIGS. 6, 6A, and 7, elongated tubular portion 208 retains a plurality of surgical tacks 100 and is adapted to drive surgical tacks 100 into tissue. As seen in FIGS. 6 and 7, elongated tubular portion 208 can be or include a generally tubular sleeve 210 defining a bore 212 therethrough, a jacket 214 having a main channel 215 and which is preferably brazed or welded to an inner surface 216 of tubular sleeve 210, and a rotatable drive rod 218 having protruding helical threads and extending concentrically longitudinally through tubular sleeve 210 and main channel 215 of jacket 214. While jacket 214 has been disclosed as being brazed or welded within tubular sleeve 210, it is envisioned that any means for fixing jacket 214 within tubular sleeve 210 can be used, for example, peening, gluing, male/female fixation or attachment, etc. Alternately, jacket 214 and tubular sleeve 210 may be of unitary construction.

Main channel 215 of jacket 214 includes a pair of longitudinally extending sub channels 220 formed into an inner surface of main channel 215. Each sub channel 220 preferably extends substantially the entire length of tubular sleeve 210 and is adapted to receive at least a portion of a respective one of legs 102 of surgical tack 100 therein. Preferably, sub channels 220 are oriented 180 degrees apart. However, it is envisioned that the radial angular orientation of the pair of sub channels 220 can be any radial distance. Depending on the radial angular orientation of the pair of sub channels 220, the radial angular length of arcuate cross member 104 is selected such that each leg 102 of surgical tack 100 is received in a respective one of said pair of sub channels 220. Accordingly, it is envisioned that if the radial angular length between the pair of sub channels 220 is less than 180 degrees, two pairs of longitudinally extending sub channels (not shown) can be formed along the inner surface of jacket 214 such that two offset columns of surgical tacks 100 can be arranged within and applied from the same elongate tubular portion 208, even substantially simultaneously.

Another embodiment for providing a supply of surgical tacks 100 includes providing interchangeable or replaceable tubular portions 208. Interchangeable tubular portions 208 may have threaded connections for attachment to housing 202 of tack applier 200. In addition, quick-release connections that are known in the art may also be used for attaching tubular portion 208 to tack applier 200. An alternate embodiment includes cassettes or other easily replaceable containers or cartridges containing a quantity of surgical tacks 100 that are configured and adapted for feeding surgical tacks 100 to drive rod 218. Preferably, the replaceable items would include drive rod 218, with tacks 100 engaged its helical threads and jacket 214 encompassing the tacks and rod. Clips, screws, snaps, and other suitable means can be employed for removably attaching jacket 214 to tubular portion 208.

Drive rod 218 preferably includes a thread 224 extending longitudinally along the entire outer surface thereof. Thread 224 defines a helical groove 226 having a depth and a pitch selected to receive arcuate cross member 104 of surgical tack 100 therein. Preferably, surgical tacks 100 will be adapted such that each of the pair of legs 102 is received in a respective sub channel 220 of jacket 214 and such that the angle φ of the arcuate cross member 104 with respect to legs 102 is equal to the pitch of thread 224.

As best shown in FIG. 6, a plurality of surgical tacks 100 may be arranged longitudinally along the length of drive rod 218 with each surgical tack 100 having a respective leg 102 positioned within a respective sub channel 220 and arcuate cross member 104 positioned within helical groove 226. In this loaded position, surgical tack 100 is defined as being in a pre-formed configuration and ready for use.

The operation of tack applier 200 is best seen with reference to FIGS. 6 and 7. Initially as seen in FIG. 6, the distal end of elongate tubular portion 208 is pressed into contact against surgical mesh M and body tissue T. Drive rod 218 is then rotated by squeezing trigger 206 against handle portion 204. Since legs 102 of surgical tack 100 are seated within sub channels 220 of jacket 214, surgical tacks 100 are prevented from rotating together with drive rod 218 within jacket 214 and tubular sleeve 210 and surgical tack 100 is moved distally and eventually expelled therefrom. Meanwhile, arcuate cross member 104 of surgical tack 100 is seated within helical groove 226 thereby causing surgical tack 100 to be advanced distally through tubular sleeve 210 by the rotational force applied to surgical tacks 100 by drive rod 218. Initially, as the pair of legs 102 of surgical tack 100 is driven through surgical mesh M and into body tissue T, the legs 102 remain parallel to one another. Left alone, the legs will tend to remain in that disposition as they are driven into the mesh and tissue. However, as surgical tack 100 advances further into body tissue T by exiting distal tip 234 of tubular portion 208, each leg 102 can be deflected by an optimal radially inwardly tapered or concavely curved lip "L" (dashed line) toward centerline 120 of surgical tack 100 defining a formed configuration of surgical tack 100. Preferably, each tip 106 crosses centerline 120 thereby better securing surgical tack 100 in body tissue T (see FIG. 7). In other words, by the pair of legs 102 crossing one another, surgical mesh M and body tissue T are trapped therebetween. Since legs 102 are merely deflected towards one another and not deformed into a different shape, surgical tack 100 can be withdrawn from body tissue T without or with minimum damage thereto.

As discussed above, surgical tacks 100 can be formed of a shape memory material such that, when legs 102 of surgical tack 100 contact the warm body tissue T, the legs will automatically deflect towards one another or diverge away from each other. Alternatively, it is envisioned that mechanical deflecting means, e.g., lip "L" can be provided at the distal end of jacket 214 or of the elongated tubular portion 208, to urge the pair of legs 102 of surgical tack 100, whether or not made of shape memory material, towards one another as the pair of legs 102 begin to pass through surgical mesh M and begin to penetrate body tissue T.

Figure 8:
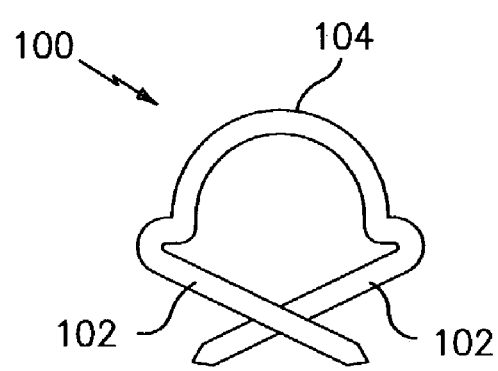
FIG. 8 is a perspective view of a surgical tack, in accordance with the present disclosure, as it would appear after having been driven into body tissue.
Figure 9:
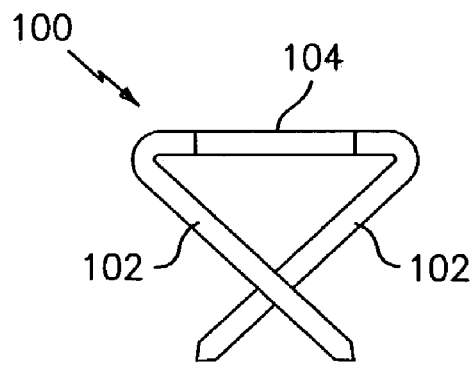
FIG. 9 is a front elevational view of the surgical tack shown in FIG. 8.
Figure 10:
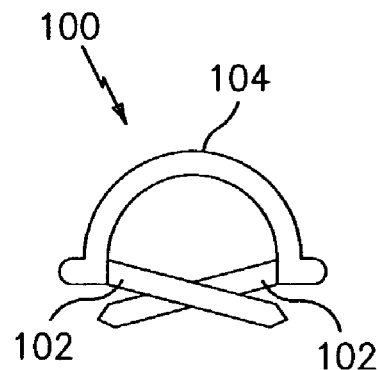
FIG. 10 is a top plan view of the surgical tack shown in FIG. 8.

FIGS. 8–10 show a surgical tack 100, after having been driven through surgical mesh M and into body tissue T and having had its legs 102 deflected towards one another. While the legs 102 have been shown as overlapping one another, it is envisioned that the pair of legs 102 can be simply brought closer to one another.

It will be understood that various modifications may be made to the embodiments disclosed herein. For example, it is envisioned that surgical tack applier 200 is provided with a removable cartridge (not shown) including a removable jacket having a drive rod and a plurality of surgical tacks 100. The jacket can be removable attached to elongated tubular member 208 by any suitable means including snaps, clips, hooks, bolts, etc. Alternatively, elongate tubular portion 208 of applier 200, that has expelled all of its surgical tacks 100, is replaceable with another tubular portion 208 filled with new surgical tacks 100. Thus, the above description should not be construed as limiting, but merely as an exemplification of preferred embodiments. Those skilled in the art will envision other modifications within the scope and spirit of the claims appended hereto.

What is claimed is:

1. A surgical fastener applier, comprising:
a housing;
an elongate tubular portion having a proximal end and a distal end, the elongate tubular portion comprising:
a bore therethrough;
an elongate jacket having an inner surface defining a longitudinal main channel extending through the jacket, the main channel being adapted to receive a surgical tack having a pair of depending legs and an arcuate cross-member interconnecting proximal ends of the legs, the main channel having an inner surface that includes a pair of longitudinally extending sub channels formed along the inner surface, each of the pair of sub channels being adapted to receive at least a portion of a respective one of a pair of legs of the surgical fastener therein;
a rotatable drive rod having a proximal end and a distal end, the drive rod extending axially through the jacket, the drive rod including a longitudinally extending helical thread, the helical thread defining a groove that is adapted to receive the arcuate cross-member of the surgical fastener therein; and
a mechanism operatively connected to the drive rod for rotating the drive rod to drive fasteners legs first from the distal end of the drive rod and from the distal end of the tubular portion.

2. The surgical applier according to claim 1, wherein the pair of sub channels the jacket are diametrically opposed.

3. The surgical applier according to claim 1, wherein the jacket includes a plurality of pairs of sub channels formed along the inner surface thereof, wherein each pair of sub channels is at least less than 180 degrees apart from one another.

4. The surgical applier according to claim 1, wherein the mechanism includes a trigger pivotably coupled to the surgical applier.

5. The surgical applier according to claim 1, wherein the applier further comprises a mechanical deforming means operatively coupled to a distal end of the jacket, the deforming means being adapted to deflect the pair of legs of the surgical fastener toward one another as the surgical fastener is expelled from the distal end of the elongate tubular member.

6. The surgical applier according to claim 5, wherein the mechanical deforming means includes radially inwardly directed lips.

7. A surgical fastener system comprising:
a surgical fastener having a pre-formed configuration and a formed configuration, the preformed configuration including a pair of legs and an arcuate cross-member interconnecting proximal ends of the legs; and
a surgical fastener applier including,
a housing having a reciprocating mechanism adapted for advancing the surgical fastener,
an elongate tubular portion extending from the housing and having a bore therethrough;
a jacket disposed within the bore and fixed to the elongate tubular portion, the jacket having an inner surface defining a longitudinally extending main channel extending therethrough and including a pair of longitudinally extending sub channels formed along the inner surface, each of the sub channels being configured and adapted to receive at least a portion of a respective one of a pair of legs of the surgical fastener in the pre-formed configuration therein, and
a rotatable drive rod operatively coupled to the reciprocating mechanism and extending axially through the main channel of the jacket, the drive rod including a helical thread extending longitudinally along a length thereof, the helical thread defining a groove therein, the groove being adapted to receive the arcuate cross-member of the surgical. fastener therein and, by rotating, to advance the surgical fastener distally through the tubular portion, the surgical fastener exiting the distal end of the tubular portion in the formed configuration.

8. The surgical fastener system of claim 7, wherein the drive rod is adapted to receive a plurality of the surgical fasteners in the pre-formed configuration.

9. The surgical fastener system of claim 8, wherein the drive rod is releasably attached to the reciprocating mechanism.

10. The surgical fastener system of claim 7, wherein the surgical fastener applier is adapted and configured to releasably receive a cassette, the cassette including a quantity of the surgical fasteners in the pre-formed configuration.

11. The surgical fastener system of claim 9, wherein the reciprocating mechanism is a trigger pivotably coupled to the housing.

12. The surgical fastener system of claim 7, wherein the applier has a distal end and a mechanical deforming means disposed at the distal end of the applier.

13. A surgical fastener applier, comprising:
a housing;
a surgical fastener having a pair of legs;
an elongate tubular portion having a proximal end and a distal end, the tubular portion having an elongate channel, the channel having an inner surface and a pair of longitudinally extending sub channels formed into and along an inner surface, each of the sub channels being adapted to receive at least a portion of a respective one of the legs of the surgical fastener therein;
a rotatable drive rod having a proximal end and a distal end, the drive rod extending axially through the elongate channel, the drive rod including a longitudinally extending helical thread, the helical thread defining a groove that is adapted to receive an arcuate cross-member of the surgical fastener therein; and
a mechanism operatively connected to the drive rod for rotating the drive rod to drive fasteners legs first from the distal end of the drive rod and from the distal end of the tubular portion.

14. The surgical applier according to claim 13, wherein the pair of sub channels of are diametrically opposed.

15. The surgical applier according to claim 13, wherein the elongate channel includes a plurality of pairs of sub channels formed along an inner surface thereof, wherein each pair of sub channels is at least less than 180 degrees apart from one another.

16. The surgical applier according to claim 13, wherein the mechanism includes a trigger pivotably coupled to the surgical applier.

17. The surgical applier according to claim 13, wherein the applier further comprises a mechanical deforming means operatively coupled to a distal end of the elongate tubular portion, the deforming means is adapted to deflect the pair of legs of the surgical fastener toward one another as the surgical fastener is expelled from the distal end of the elongate tubular member.

18. The surgical applier according to claim 17, wherein the mechanical deforming means includes radially inwardly directed lips.

* * * * *